(12) United States Patent
Iftime et al.

(10) Patent No.: US 8,629,414 B2
(45) Date of Patent: Jan. 14, 2014

(54) CLEAR OVERCOAT COMPOSITIONS AND METHODS FOR USING AND DETECTING THE SAME

(75) Inventors: Gabriel Iftime, Mississauga (CA);
Martin E. Hoover, Rochester, NY (US);
Peter G. Odell, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 44 days.

(21) Appl. No.: 13/085,384

(22) Filed: Apr. 12, 2011

(65) Prior Publication Data
US 2012/0261592 A1 Oct. 18, 2012

(51) Int. Cl.
*G01T 1/10* (2006.01)

(52) U.S. Cl.
USPC .................. 250/473.1; 250/301; 250/302

(58) Field of Classification Search
USPC .................. 250/473.1, 301, 302, 303
See application file for complete search history.

(56) References Cited

U.S. PATENT DOCUMENTS

| | | | |
|---|---|---|---|
| 4,157,784 A * | 6/1979 | Grottrup et al. ............. 235/491 |
| 5,122,187 A | 6/1992 | Schwarz et al. | |
| 6,059,871 A * | 5/2000 | Boils et al. ................. 106/31.57 |
| 6,906,118 B2 | 6/2005 | Goodbrand et al. | |
| 6,946,515 B1 * | 9/2005 | Lettmann et al. ............. 524/591 |
| 7,674,326 B2 | 3/2010 | Iftime et al. | |
| 7,690,746 B2 | 4/2010 | Mantell et al. | |
| 2003/0114557 A1 * | 6/2003 | Lin et al. ......................... 524/91 |
| 2008/0090928 A1 | 4/2008 | Iftime et al. | |
| 2008/0124498 A1 * | 5/2008 | Cole et al. ....................... 428/29 |
| 2008/0145777 A1 * | 6/2008 | Iftime et al. .................. 430/114 |
| 2009/0195572 A1 | 8/2009 | Kovacs et al. | |
| 2010/0108172 A1 * | 5/2010 | Liu et al. ....................... 138/137 |

OTHER PUBLICATIONS

U.S. Appl. No. 12/757,415, filed Apr. 9, 2010, to Michelle N. Chretien et al.

* cited by examiner

*Primary Examiner* — Christine Sung
(74) *Attorney, Agent, or Firm* — Pillsbury Winthrop Shaw Pittman LLP

(57) ABSTRACT

Present embodiments generally relate to a novel clear or colorless overcoat composition that may be used for overcoating, for example, ink based images and xerographic images. The overcoat composition, which may be used as a base for a clear solid ink, comprises one or more ultraviolet (UV) absorbing additives. Also included in the present embodiments is a method for using and detecting the overcoat composition in connection with a substrate, for example, a substrate that includes printed images thereon.

19 Claims, 4 Drawing Sheets

CLEAR OVERCOAT COMPOSITIONS AND METHODS FOR USING AND DETECTING THE SAME

CROSS REFERENCE TO RELATED APPLICATIONS

Reference is made to commonly owned and co-pending, U.S. patent application Ser. No. 13/085,365, filed electronically on the same day as the present application, entitled, "Clear Overcoat Compositions and Method for Stabilizing the Same", the entire disclosure of which is incorporated herein by reference in its entirety.

BACKGROUND

The present disclosure generally relates to a clear or substantially colorless overcoat composition that may be used for overcoating, for example, ink based images and xerographic images. The overcoat composition described herein is a clear solid ink which comprises one or more ultraviolet (UV) absorbing additives. Also described is a method and systems for using and detecting the overcoat composition in connection with a substrate, for example, a substrate that includes printed images thereon.

Wax based inks, sometimes known as phase change inks or solid inks, are used to form digital images on paper using heated piezoelectric or acoustic ink jet heads. The ejection of an ink drop by the print heads is electronically controlled. In embodiments, the hot drop partially cools upon hitting an intermediate surface, often an aluminum drum. The complete image is assembled on the intermediate surface and then transferred to paper and fixed thereon with a combination of pressure and heat resulting in a solid ink, or wax-based ink print. Alternatively, the wax-based image can be printed directly to the substrate. The direct-to-paper image is also exposed to a combination of pressure and heat to fix the image to the substrate.

Known methods of protecting ink or toner-based images include applying an overcoat composition to the substrate. Both surfaces, however, can be difficult to subsequently coat. In addition, the coating of prints made with solid ink or wax-based ink can be especially difficult due to the fact that the robustness of such prints is relatively poor when compared to inkjet or xerographic prints. This fact raises a significant challenge in applications used in the advertising mail, or "direct-mail," market. The conventional approach in direct-mail application is to overcoat the text with clear ink text image that is registered to the visible image, which requires printing and registration of the clear color in the same manner as that used with other colors (e.g., cyan (c), magenta (m), yellow (y), black (k)). With colors, the printing and registration is achieved with certain systems, such as for example, an Image-on-web-array (IOWA) inline scanning sensor, which are configured to detect visible colors. The problem with using the clear ink with such systems, however, is that the clear ink is undetectable since it is clear. Thus, the current systems require a clear solid ink that is detectable.

To address the above issues, previous proposed methods used either fluorescent or infrared (IR) sensitive materials in the clear overcoat ink compositions, as disclosed in U.S. Pat. No. 7,690,746, which is hereby incorporated by reference. However, fluorescent materials have several disadvantages, such as high cost—particularly of clear fluorescent dyes, poor contrast on white bright paper, and poor thermal stability. IR dyes also have disadvantages, such as poor solubility in low polarity media like solid ink base. IR dyes are also never truly invisible in normal light conditions which renders the clear overcoat composition visible. Alternatively, U.S. patent application Ser. No. 12/757,415 to Michelle N. Chretien et al., filed on Apr. 9, 2010, which is hereby incorporated by reference, proposes the use of fluorescence measurement of paper substrates through the use of a clear UV gel ink. However, this method does not work with clear solid ink overcoat compositions because the solid ink does not have any absorption when exposed to black light, a currently easily available UV light.

Thus, there remains a need for an overcoat composition that can be used for protecting solid ink and toner-based images, which provides overcoat coating properties including, for example, thermal and light stability, scratch resistance, and smear (or rub) resistance to toner-based images and ink-based images, particularly in commercial print applications, and which can also be detected by scanning sensors used in current printing and registration systems.

SUMMARY

According to embodiments illustrated herein, there is provided an overcoating composition and methods of use with ink based and xerographic prints.

In one embodiment, there is disclosed a method for detecting a clear overcoat composition used to protect ink-based or toner-based images, comprising: providing a clear overcoat composition further comprising an ink vehicle, and an ultraviolet absorbing additive; applying the clear overcoat composition to an ink-based or toner-based image on a substrate, wherein the substrate includes an optical brightener; exposing the overcoated image to an ultraviolet light source, thereby activating the optical brightener in the substrate to create a contrast image; evaluating the overcoated image with an image sensor for any activation to detect the presence of the ultraviolet absorbing additive.

In another embodiment, there is provided a method for detecting a clear overcoat composition used to protect ink-based or toner-based images, comprising: providing a clear overcoat composition further comprising an ink vehicle, and an ultraviolet absorbing additive; applying the clear overcoat composition to an ink-based or toner-based image on a substrate, wherein the substrate includes an optical brightener; exposing the overcoated image to an activating radiation having a wavelength that excites the optical brightener and is absorbed by the ultraviolet absorbing additive, whereby the activating radiation activates the optical brightener in the substrate and is blocked by the ultraviolet absorbing additive in the overcoat composition; evaluating the protected image with an image sensor for any activation to detect the presence of the ultraviolet absorbing additive.

In yet another embodiment, there is provided a method for detecting a printed image, comprising: providing a clear solid ink composition further comprising an ink vehicle, and an ultraviolet absorbing additive; applying the clear solid ink composition on a substrate to form a printed image, wherein the substrate includes an optical brightener; exposing the printed image to an ultraviolet light source, thereby activating the optical brightener in the substrate to create a contrast image; evaluating the protected image with an image sensor for any activation to detect the presence of the ultraviolet absorbing additive.

In yet further embodiments, there is provided a clear solid ink composition comprising: an ink vehicle, and an ultraviolet absorbing additive, wherein the ultraviolet absorbing additive is selected from the group consisting of hydroxyphenyl benzotriazole, hydroxyphenyl triazines, substituted benzophenones, substituted cinnamates and mixtures thereof and is present in the clear solid ink composition in an amount of from about 0.1 to about 10 percent by weight of the total weight of the clear solid ink composition.

BRIEF DESCRIPTION OF THE DRAWINGS

For a better understanding, reference may be had to the accompanying figure.

Unless otherwise noted, the same reference numeral in different Figures refers to the same or similar feature.

DETAILED DESCRIPTION

Figure 1:
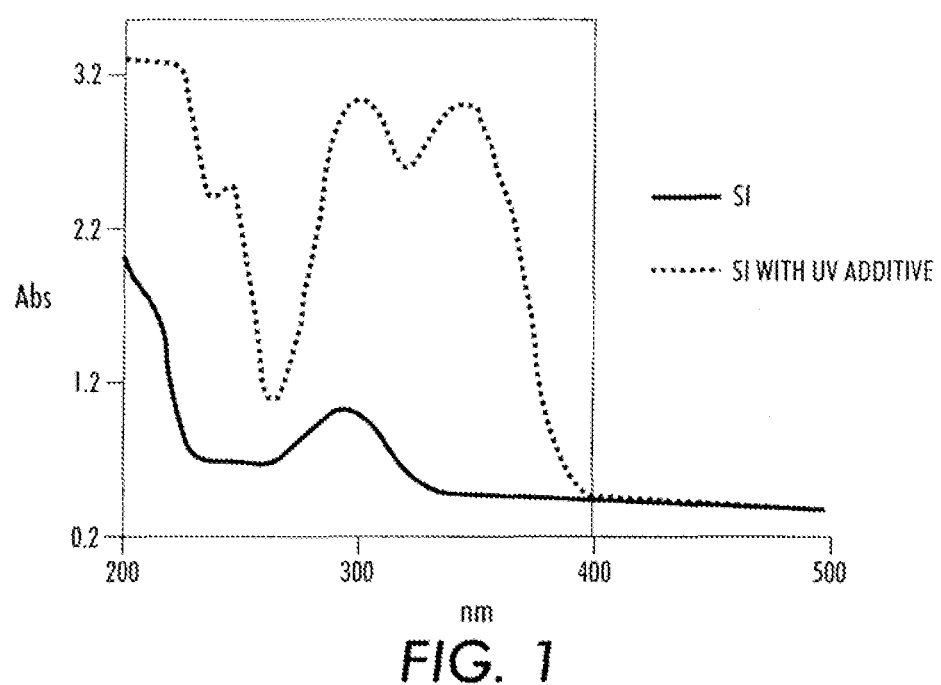
FIG. 1 is a graph illustrating the difference in absorption of a clear base ink (SD with and without UV absorbing additives.

As explained above, there remains a need for an overcoat composition that can be used for protecting solid ink and toner-based images, which provides overcoat coating properties including, for example, thermal and light stability, scratch resistance, and smear (or rub) resistance to toner-based images and ink-based images, particularly in commercial print applications, and which can also be detected by scanning sensors used in current printing and registration systems. In embodiments, the overcoat composition is used as part of a base for a solid ink. In key markets, such as those involving direct-mail applications, prints must maintain high image quality throughout the mail handling process. Current solid ink does not meet such requirements. More generally, the robustness of prints made with commercial solid ink today is relatively poor when compared with inkjet or xerographic prints. As such, the present embodiments resolves these issues through the use of a clear or substantially colorless overcoat composition which is coated onto the particular image which requires protection. For direct mail, this means to overcoat specific text which requires protection, for example, the address and name of the mail recipient, with the clear overcoat composition.

Like with CMYK colors, the clear overcoat layer requires calibration during the printing process in order to ensure consistent high quality prints. With colors, this is currently achieved with systems, such as the IOWA inline scanning sensor, which are able to detect visible colors. This enables color registration head alignment, missing jet detection, uniformity detection, and the like. One obstacle to using such clear overcoat composition, however, is that the clear composition is undetectable with systems such as IOWA and there is no possibility to ensure consistent overcoat prints with these current systems. The systems require a clear overcoat composition that is detectable when needed but without having any detrimental effect with respect to the clear color of the overcoat. As discussed above, previous methods proposed use of either fluorescent or IR sensitive materials in the clear overcoat composition, but these materials suffered from several disadvantages. Other methods employed clear UV gel overcoat compositions but were shown not to work with solid ink base because the compositions failed to show any contrast on white paper as they lacked any absorption at the exposing wavelength (could not be detected with black light (365 nm UV light)). Thus, such solid ink overcoat compositions could not be calibrated with an IOWA system.

The present embodiments overcomes the above-described problems by using a clear overcoat composition which comprises a solid ink base material made by adding an UV absorbing clear additive into the solid ink base material. The additive provides an ink with a very high absorption at the excitation wavelength. As such, the overcoat composition is easily detectable with UV light, such as black light, when printed on a substrate containing some optical brightener agent. Unlike fluorescent additives, the UV absorbing additive blocks incident UV light but it is not actually excited by the UV light. The contrast necessary for detection is provided because the optical brightener from the substrate is activated by the incident UV light and emits light typically blue. Commonly used white papers, like XEROX 4200, contain such optical brighteners.

An optical brightener is a clear or colorless material which emits blue or green light when subjected to incident UV light. In other words, an optical brightener is a colorless fluorescent material. Optical brighteners are extensively used as additives the paper substrates because the emitted light compensates for potential yellowing of the substrate, providing bright substrates, either on white or pastel colors papers. In plastics they are used to provide a bright appearance toward white. There are approximately 400 examples of known optical brighteners identified by Color Index International (CI) at www.colour-index.org. Basic class types of optical brighteners include, for example, triazine-stilbenes (di-, tetra- or hexa-sulfonated), coumarins, imidazolines, diazoles, triazoles, benzoxazolines, biphenyl-stilbenes, and the like.

When exposed to UV light, the white sheet of paper emits strong blue light as the optical brighteners in the paper is excited by the UV light. Consequently, an area printed with an solid ink base material containing UV absorbing additive on white bright paper will appear colorless under normal viewing light but will appear dark over, a bright blue background—providing for excellent viewing contrast and allowing for detection of the clear overcoat composition for use in the IOWA calibration process so long as the system is equipped with a UV light source, such as black light. Black light sources are readily available and do not present safety issues. Thus, the present embodiments provide immediate benefits of significant cost reduction and ease of implementation as compared with the prior art.

The overcoat composition disclosed herein is clear or substantially colorless. As used herein, "substantially colorless" refers to the overcoat composition being substantially or completely transparent or clear upon viewing. For this, the composition may be substantially free of colorants.

Suitable UV absorbing additives have a strong absorption in the UV range of the spectrum, generally comprised of wavelengths below 400 nm, or from about 330 nm to about 400 nm. Of particular interest are the embodiments comprising UV absorbing additives that have a strong absorption in the spectrum range of from about 330 nm to about 400 nm since those additives are efficient absorbers of UV light emitted by the UV black light sources which operate at wavelengths of from about 350 nm and higher.

In the present embodiments, clear ink overcoat compositions having an amount of UV absorbing additives, such as for example, from the hydroxyphenyl benzotriazole class of compounds, were demonstrated to be detectable with the IOWA system. In specific embodiments, it was shown that a clear ink overcoat composition having about 2 weight percent of 2-(2H-benzotriazol-2-yl)-p-cresol, which is a phenol substituted benzotriazole (also available as TINUVIN P light absorbing material from Ciba Specialty Chemicals (Basel, Switzerland)), was detectable. Other UV absorbing additives include, for example, other hydroxyphenyl substituted benzotriazoles like other TINUVIN materials available from CIBA. Examples include TINUVIN 123, 326, 171, 234, 328, 2-(2-hydroxy-3,5-di(1,1-dimethylbenzyl))-2H-benzotriazole commercialized as LOWILITE 234 by the Great Lakes Chemical Corporation. Other benzotriazoles include LOWILITE 26, 27, 28, 29 and 35 all available from the Great Lakes Chemical Company. and the like and mixtures thereof. Other suitable materials are hydroxyphenyl substituted triazines like bis-ethylhexyloxyphenol methoxyphenyl triazine) marketed as Tinosorb S by BASF; substituted cinnamates like Octyl methoxycinnamate available under the trade name of Tinosorb OMC; substituted benzophenone materials like for example, 2-hydroxy-4-methoxybenzophenone, commercialized under the name of LOWILITE 20 by the Great Lakes Chemical Corporation in Michigan, USA, currently part of Chemtura Corporation. I In embodiments, the UV absorbing additive is present in the overcoat composition in an amount of from about 0.01 to about 50 weight percent, or from about 0.1 to about 10 weight percent, or from about 0.2 to about 5 weight percent of the total weight of the overcoat composition. For comparison, samples made with clear overcoat compositions without the additives could simply not be detected with UV light, such as black light (UV light @ 365 nm). In contrast, the overcoat samples containing the UV absorbing additives were completely detectable when printed on white paper (XEROX 4200) as well as on various colored paper (XEROX Pastel). The present embodiments are particularly advantageous when used with white paper substrates, providing excellent contrast. For comparison, samples made with fluorescent additives showed poor contrast on white paper because their fluorescence is masked or overwhelmed by the blue fluorescence of the white paper. Of the fluorescent additives, only red emitting dyes showed some contrast. Thus, the present embodiments provide an easy and very efficient solution for providing detectability of clear solid ink overcoat compositions. The present embodiments thus provide numerous advantages over the prior art, such as, significant cost reduction, as the UV absorbing additives are much less expensive as compared to fluorescent and IR dyes, chemical and thermal stability, excellent solubility with clear ink base, best contrast on white paper substrates, detectability on both colored paper and high yield paper, and truly invisible under normal light use conditions.

The clear ink overcoat composition typically comprises at least an ink vehicle or binder and at least one UV absorbing additive. The vehicle may include one selected from the group consisting of ethylene/propylene copolymers, urethane derivates of oxidized synthetic or petroleum waxes, n-paraffinic hydrocarbons, branched paraffinic hydrocarbons, naphthenic hydrocarbons, highly branched hydrocarbons, ethoxylated alcohols, linear alcohols, hydrocarbon-based waxes, modified maleic anhydride hydrocarbon adducts of polyolefins prepared by graft copolymerization, mixtures of monoamides and tretraamides, and mixtures thereof. The vehicle may also be any of those described in U.S. Pat. Nos. 7,674, 326; 6,906,118 and/or 5,122,187, each incorporated herein by reference in its entirety. The ink vehicle may also be UV radiation curable, for example, one selected from the group consisting of paraffins, microcrystalline waxes, polyethylene waxes, ester waxes, fatty acids, fatty amide containing materials, sulfonamide materials, ethoxylated alcohols, linear alcohols, and combinations thereof, or any of the ink vehicles described in U.S. Patent Publication No. 2008/0090928, incorporated herein by reference in its entirety.

The ink vehicle may also include a wax such as paraffins, microcrystalline waxes, polyolefin waxes such as polyethylene or polypropylene waxes, ester waxes, fatty acids and other waxy materials, fatty amide containing materials, sulfonamide materials, resinous materials made from different natural sources (tall oil rosins and rosin esters, for example), and synthetic waxes. The wax may be present in an amount of from about 5% to about 25% by weight of the ink. Examples of suitable waxes include polypropylenes and polyethylenes commercially available from Allied Chemical and Petrolite Corporation, wax emulsions available from Michaelman Inc. and the Daniels Products Company, EPOLENE N-15 commercially available from Eastman Chemical Products, Inc., VISCOL 550-P, a low weight average molecular weight polypropylene available from Sanyo Kasei K.K., and similar materials. The commercially available polyethylenes selected usually possess a molecular weight of from about 1,000 to about 1,500, while the commercially available polypropylenes utilized for the toner compositions of the present invention are believed to have a molecular weight of from about 4,000 to about 5,000. Examples of suitable functionalized waxes include, for example, amines, amides, imides, esters, quaternary amines, carboxylic acids or acrylic polymer emulsion, for example JONCRYL 74, 89, 130, 537, and 538, all available from SC Johnson Wax, chlorinated polypropylenes and polyethylenes commercially available from Allied Chemical and Petrolite Corporation and SC Johnson wax.

The overcoat compositions of the present embodiments may further include conventional additives to take advantage of the known functionality associated with such conventional additives. Such additives may include, for example, defoamers, slip and leveling agents, and the like.

The overcoat composition of the present embodiments may be jetted directly onto the image receiving substrate. The overcoat composition may then be leveled by contact or non-contact leveling, for example as disclosed in U.S. Patent Publication No. 2009/0195572. The present embodiments may be used in a transfix inkjet device, such as, for example, a solid inkjet printer, an inkjet printer, or an inkjet facsimile machine, which use an intermediate substrate. However, the systems and methods herein are equally applicable to direct printing systems where the images are jetted directly onto image receiving media without use of an intermediate substrate. The systems and methods herein will also include use of a radiation emitting source, which emits radiation, or light, having a wavelength at which the UV absorbing additive absorbs the radiation, thereby activating the optical brightener and being blocked by the additive. In embodiments, the radiation emitting source produces an activating radiation that has a wavelength in the range of from about 300 to about 400 nm. In this manner, the presence or absence of the clear ink overcoat composition can subsequently be detected by an image sensor, and the amount of the ink due to relative intensity.

The overcoat compositions of the present disclosure can be used in image processing comprising generating an ink-based or toner-based image on a substrate, following the generation of the image, ink jetting the overcoat composition onto the substrate as a whole, onto the image as a whole, onto part(s) of the image, onto part(s) of the substrate, or any combination thereof, and curing the overcoat composition.

The substrate employed can be any appropriate substrate containing some optical brightener additive, depending upon the end use of the print. Exemplary substrates include, but are not limited to, plain paper, coated paper, plastics, polymeric films, treated cellulosics, wood, xerographic substrates, ceramics, fibers, metals and mixtures thereof, optionally comprising additives coated thereon.

When coating a toner-based image, the fused toner-based print is obtained first and then subjected to an ink jet printer containing the jettable overcoat composition. The toner-based print can be prepared by any suitable conventional xerographic technique or variant thereof. Similarly, when coating an ink-based image, the ink-based image is generated first and then subjected to an ink jet printer containing the jettable overcoat composition. If the ink-based image is formed using an ink jet printer, then the ink-based image can be subjected to a separate ink jet printer containing the jettable overcoat composition or the ink jet ink can be housed in the same ink jet printer as the composition, whereby the composition is coated onto the substrate and/or image as a colorless, transparent fluid after the ink jet ink image is formed. When the overcoat composition is coated over an ink-based image, particularly, an image produced using an ink jet printer, the image can be prepared by any suitable conventional process or variant thereof. When the overcoat composition is part of a solid ink, an ink-based image is simply generated by directly applying the solid ink composition to a substrate. Thus, the ink-based image will already include the overcoat composition upon formation.

When the composition is coated onto an image, parts thereof, substrate, and/or parts thereof, it can be applied at different levels of resolution. For example, the composition can be applied at the resolution of the print halftone dot, at the resolution of distinct part(s) of the image, or at a little less resolution than distinct part(s) of the image, allowing for some overlap of the composition onto nonimaged areas of the substrate. The typical composition deposition level is in an amount of from about 5 to about 50 picoliters drop size. The composition can be applied in at least one pass over the image at any stage in the image formation using any known ink jet printing technique, such as, for example, drop-on-demand ink jet printing including, but not limited to, piezoelectric and acoustic ink jet printing. The application of the composition can be controlled with the same information used to form the image such that only one digital file is needed to produce the image and the overcoat composition. Thus, the overcoat composition is fully digital.

Various exemplary embodiments encompassed herein include a method of imaging which includes generating an electrostatic latent image on an imaging member, developing a latent image, and transferring the developed electrostatic image to a suitable substrate.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLES

The example set forth herein below and is illustrative of different compositions and conditions that can be used in practicing the present embodiments. All proportions are by weight unless otherwise indicated. It will be apparent, however, that the embodiments can be practiced with many types of compositions and can have many different uses in accordance with the disclosure above and as pointed out hereinafter.

Comparative Example

Lack of Detection of Conventional Clear Solid Ink Overcoat (UV VIS Absorption Spectra)

Samples of conventional clear overcoat solid ink base (SI) made from a phase change material consisting of a long chains alcohol (mixtures containing from 30 to 70 carbon atoms) with a melting point of about 100° C. without and with UV additive (TINUVIN P) were made by placing melt compositions in between quartz slides with 5 microns spacers.

As shown in FIG. 1, the clear base ink (SI) has essentially no absorption at the detecting wavelength (UV @365 nm). On the contrary, when 2% of TINUVIN P (UV absorbing additive) was added, the new ink has huge absorption in the UV range (red line). As a result, one would expect that the sample with no additive (as is) will show no contrast when printed on white paper (no detectability).

Detection Tests

Lines were traced on white paper (XEROX 4200) and yellow paper (XEROX Pastel) substrates with clear ink base (the phase change ink base used in Xerox Color Qube printers) and with clear solid ink overcoat base and were compared for detection with a clear overcoat made by using a TINUVIN P as an UV absorbing additive (identified as (a) in Table 1 below).

Figure 2:
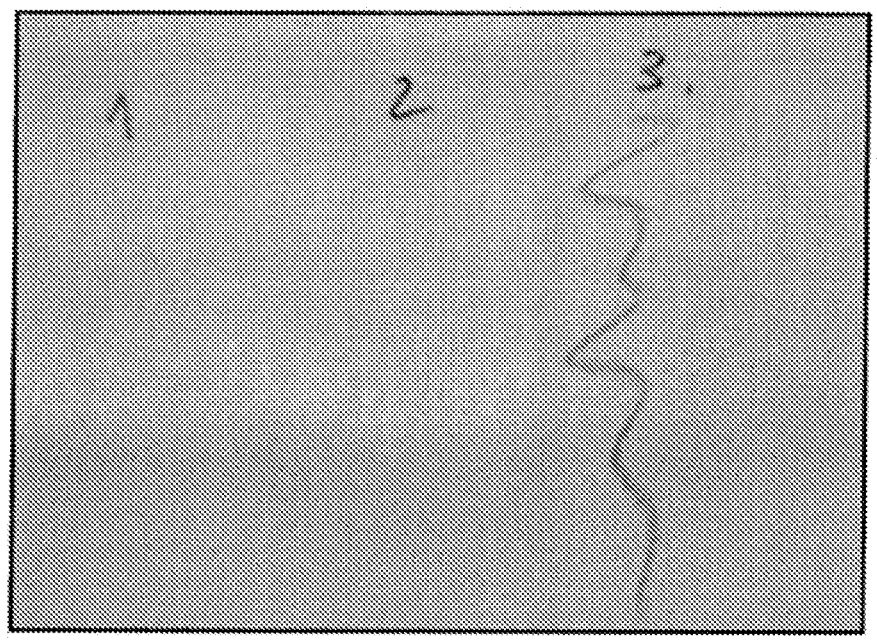
FIG. 2 is a photograph demonstrating the differences in detectability under black light of clear ink overcoat compositions with and without UV absorbing additives.

Lines were traced in the following order from left to right, as shown in FIG. 2: (1) Color Qube solid ink clear base; (2) conventional clear solid ink overcoat; and (3) conventional clear solid ink overcoat with TINUVIN additive (identified as (a) in Table 1 below). Samples were exposed to black light for detection. FIG. 2 shows absolutely no contrast (no detection) of the lines (1) and (2) both on white paper and yellow paper. Only sample (3), with the additive according to the present embodiments, was detectable.

Example 1

Inks Preparation

After confirming lack of detectability of conventional solid ink overcoat materials, as shown in the above Comparative Example, the focus was shifted to developing a detectable solid ink overcoat and comparing its efficiency with previously reported fluorescent dye additive approach.

Several clear ink compositions with "detectable" additives were prepared by dissolving 0.100 g of additive in 9.900 g of molten clear ink base on a hotplate and stirring. The process produced uniformly dispersed clear inks which were further evaluated. For comparison, UV absorbing additive samples as well as samples made with clear fluorescent additives were prepared. In addition, two types of clear ink were used: first the conventional clear overcoat composition (based on phase change materials with a melting point of about 100° C. and second, the currently commercialized Color Qube ink base. Table 1 lists the inks that were prepared.

TABLE 1

| Ink # | Additive | Type | Ink base | Comments |
|---|---|---|---|---|
| a | TINUVIN P | UV Absorbing (from CIBA) | Clear Overcoat | UV Absorbing (present embodiments) |
| b | DFSB-C0 | Clear/Blue fluorescent (from Risk Reactor) | Clear Overcoat | Lost Fluorescence |
| c | UVITEX OB | Clear/Blue fluorescent (from Risk Reactor) | Clear Overcoat | Lost Fluorescence |
| d | DFSB-C0 | Clear/Blue fluorescent (from Risk Reactor) | ColorQube Ink Base | Blue Fluorescence |
| e | 2-(2-Hydroxyphenyl)-benzothiazole | Clear/Green fluorescent (from Sigma Aldrich) | Clear Overcoat | Green Fluorescence |
| f | DFKY-C7 | Clear/Red fluorescent | Clear Overcoat | Red Fluorescence |

The surprising observation was that inks made with Clear Blue fluorescent dyes (identified as (b) and (c) in Table I) were not fluorescent in the clear overcoat base. Since the clear overcoat base materials do not absorb light at the 360 nm (used for detection) quenching is not believed to be the cause. It is likely that the phase change material from the clear overcoat which is a substituted long chain alkyl material, reacted with the fluorescent dyes and this resulted in their degradation. As a result, these dyes are useless for detection by fluorescence. For this reason, samples were prepared with Color Qube base (identified as (d) in Table 1) and fluorescence was observed, as expected. Thus, using the Color Qube base allowed comparison of the blue fluorescent dye concept with the UV absorbing additives. This occurrence illustrates an issue with fluorescent dyes—chemical instability.

Given the small amounts of inks prepared, actual "prints" were made by hand-writing with the cooled (hard) inks. This is sufficient to illustrate the detection concept with each of the inks.

Detection

Figure 3A:
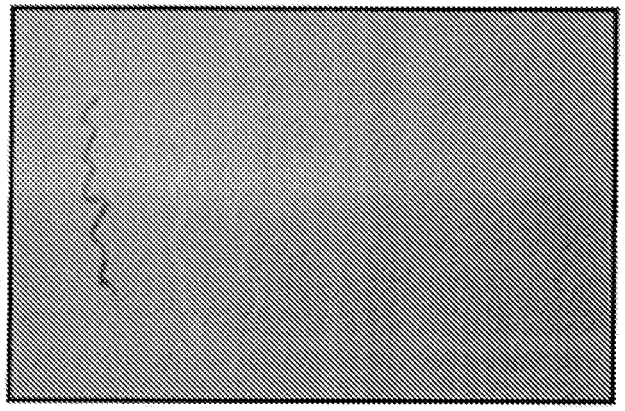
FIGS. 3A-3E are photographs demonstrating the differences in detectability under black light of various clear ink overcoat compositions with UV absorbing additives or fluorescent additives on various paper substrates.
Figure 3B:
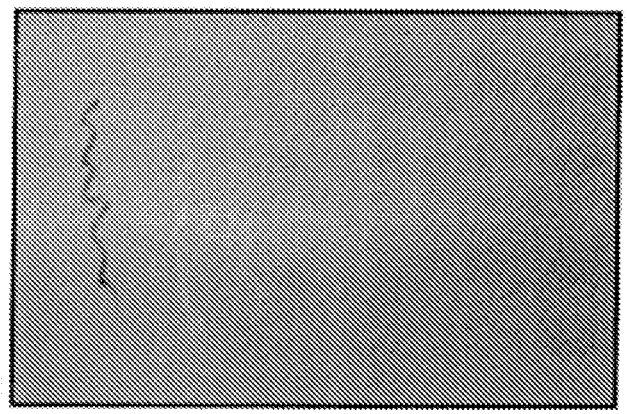
Figure 3C:
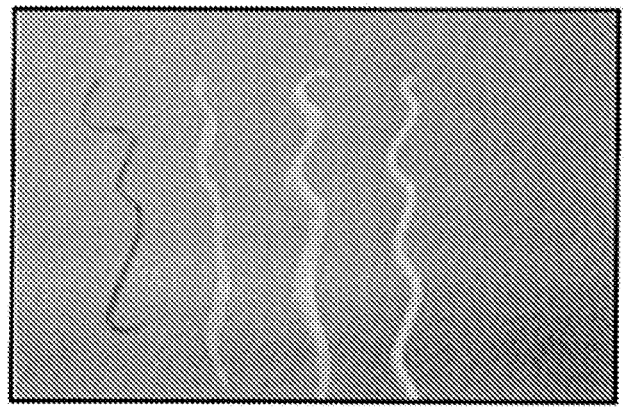
Figure 3D:
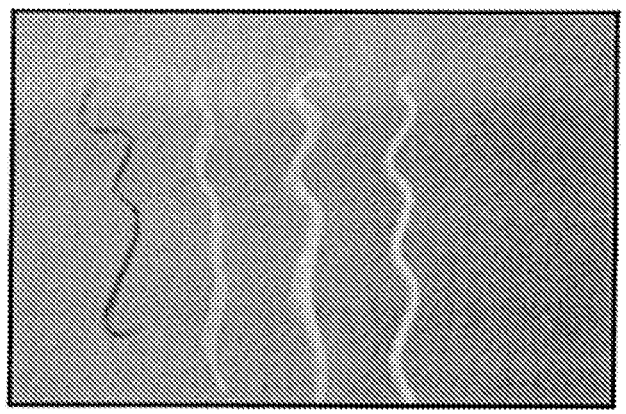
Figure 3E:
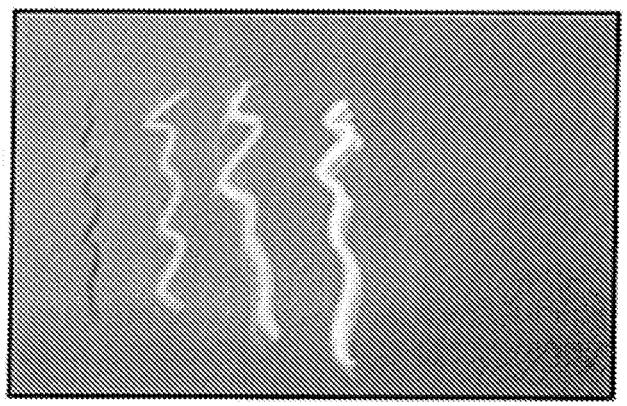

Detection was done by illumination with UV light (365 nm) which is the type of light commonly used in stores to check money. Several types of paper substrate were used: (1) White paper (XEROX 4200; high brightness) (FIG. 3A); (2) XEROX high yield business paper (lower brightness paper) (FIG. 3B); (3) XEROX Pastel Blue paper (FIG. 3C); (4) XEROX Pastel Green paper (FIG. 3D); and (5) XEROX Pastel Yellow paper (FIG. 3E).

The objective was to test detectability of various types of inks on various types of paper substrates which are preferred for applications such as direct-mail. FIGS. 3A-3E show the appearance under UV detecting light. Under normal light conditions, the "prints" (represented as simple lines) appear identical, as somewhat glossy but clear lines on all paper substrates. In all the pictures, the order of the scribbled inks is from left to right: UV absorbing (identified as (a) in Table 1); Red fluorescent (identified as (f) in Table 1); Green fluorescent (identified as (e) in Table 1); and Blue fluorescent (identified as (dd) in Table 1). All were viewed under black light.

Results

The ink containing UV absorbing additive was detectable as a dark blue line on all five types of paper substrates, both white and colored. The UV absorbing additive is particularly advantageous on white bright paper (XEROX 4200).

The fluorescent dyes are essentially hard to detect, particularly blue which cannot be seen in FIGS. 3A-3E. This occurs because the emitted fluorescence by the dyes is essentially masked by the strong blue emission by the optical brightener additives from the paper. Only red emitting dye showed some contrast. Fluorescent additives are easiest to detect on colored paper substrates (less bright because of the color). Still, none of the fluorescent additives performed as well in detectability as the UV absorbing material.

All the patents and applications referred to herein are hereby specifically, and totally incorporated herein by reference in their entirety in the instant specification.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A method for detecting an overcoated image and for protecting an underlying ink-based or toner-based image, comprising:
   providing a clear ink suitable for printing comprising
      an ink vehicle, and
      an ultraviolet absorbing additive;
   providing a substrate having an ink-based or toner-based image; wherein the substrate comprises an optical brightener;
   printing the clear ink over the ink-based or toner-based on the substrate to create a protective, overcoated image conferring scratch and smear resistance to the ink-based or toner-based image;
   exposing the substrate to an ultraviolet light source, thereby activating the optical brightener in the substrate to create a contrast image between the substrate and the overcoated image;
   evaluating the substrate for any activation of the optical brightener creating the contrast image to detect the presence of the ultraviolet absorbing additive in the overcoated image.

2. The method of claim 1, wherein the clear ink is a solid ink.

3. The method of claim 1, wherein the ink vehicle is selected from the group consisting of ethylene/propylene copolymers, urethane derivates of oxidized synthetic or petroleum waxes, n-paraffinic hydrocarbons, branched paraffinic hydrocarbons, naphthenic hydrocarbons, highly branched hydrocarbons, ethoxylated alcohols, linear alcohols, hydrocarbon-based waxes, modified maleic anhydride hydrocarbon adducts of polyolefins prepared by graft copolymerization, mixtures of monoamides and tretraamides, paraffins, microcrystalline waxes, polyethylene waxes, ester waxes, fatty acids, fatty amide containing materials, sulfonamide materials, ethoxylated alcohols, linear alcohols, polyester, polyacrylate and mixtures thereof.

4. The method of claim 1, wherein the clear ink further includes an additive selected from the group consisting of a defoamer, slip agent, leveling agent, and mixtures thereof.

5. The method of claim 1, wherein the ultraviolet absorbing additive is present in the clear ink in an amount of from about 0.01 to about 50 percent by weight of the total weight of the clear ink.

6. The method of claim 5, wherein the ultraviolet absorbing additive is present in the clear ink in an amount of from about 0.2 to about 5 percent by weight of the total weight of the clear ink.

7. The method of claim 1, wherein the ultraviolet absorbing additive is selected from the group consisting of hydroxyphenyl benzotriazoles, hydroxyphenyl triazines, substituted benzophenones, substituted cinnamates and mixtures thereof.

8. The method of claim 1, wherein the ultraviolet absorbing additive is 2-(2H-benzotriazol-2-yl)-p-cresol.

9. The method of claim 1, wherein the ultraviolet absorbing additive has an UV absorption of 400 nm or lower.

10. The method of claim 9, wherein the ultraviolet absorbing additive has an UV absorption of from about 330 nm to about 400 nm.

11. The method of claim 1, wherein the ultraviolet light source is black light.

12. The method of claim 1, wherein the substrate includes both white and colored paper.

13. A method for detecting an overcoated image and for protecting an underlying ink-based or toner-based images, comprising:
providing a clear ink suitable for printing comprising
an ink vehicle, and
an ultraviolet absorbing additive;
providing a substrate having an ink-based or toner-based image; wherein the substrate comprises an optical brightener;
printing the clear ink over the ink-based or toner-based image on the substrate to create a protective, overcoated image conferring scratch and smear resistance to the ink-based or toner-based image;
exposing the substrate to an activating radiation having a wavelength that excites the optical brightener and is absorbed by the ultraviolet absorbing additive, whereby the activating radiation activates the optical brightener in the substrate and is absorbed by the ultraviolet absorbing additive in the clear ink creating a contrast image; and
evaluating the substrate for any activation of the optical brightener creating the contrast image to detect the presence of the ultraviolet absorbing additive in the overcoated image.

14. The method of claim 13, wherein the activating radiation has a wavelength in the range of from about 300 to about 400 nm.

15. A method for detecting a printed image, comprising:
providing a clear solid ink suitable for printing comprising
an ink vehicle, and
an ultraviolet absorbing additive, wherein the ultraviolet absorbing additive is present in the clear solid ink composition in an amount of from about 0.01 to about 50 percent by weight of the total weight of the clear solid ink composition;
providing a substrate comprising an optical brightener;
printing the clear solid ink on the substrate to form a printed image;
exposing the substrate to an ultraviolet light source, thereby activating the optical brightener in the substrate to create a contrast image between the substrate and the printed image;
evaluating the substrate for any activation of the optical brightener creating the contrast image to detect the presence of the ultraviolet absorbing additive in the printed image.

16. The method of claim 15, wherein the ink vehicle is selected from the group consisting of ethylene/propylene copolymers, urethane derivates of oxidized synthetic or petroleum waxes, n-paraffinic hydrocarbons, branched paraffinic hydrocarbons, naphthenic hydrocarbons, highly branched hydrocarbons, ethoxylated alcohols, linear alcohols, hydrocarbon-based waxes, modified maleic anhydride hydrocarbon adducts of polyolefins prepared by graft copolymerization, mixtures of monoamides and tretraamides, paraffins, microcrystalline waxes, polyethylene waxes, ester waxes, fatty acids, fatty amide containing materials, sulfonamide materials, ethoxylated alcohols, linear alcohols, polyester, polyacrylate and mixtures thereof.

17. The system of claim 15, wherein the ultraviolet absorbing additive is present in the clear solid ink in an amount of from about 0.01 to about 50 percent by weight of the total weight of the clear solid ink.

18. The system of claim 17, wherein the ultraviolet absorbing additive is present in the clear solid ink in an amount of from about 0.2 to about 5 percent by weight of the total weight of the clear ink.

19. The system of claim 15, wherein the ultraviolet absorbing additive is selected from the group consisting of hydroxyphenyl benzotriazole, hydroxyphenyl triazines, substituted benzophenones, substituted cinnamates and mixtures thereof.

* * * * *